United States Patent [19]
Yoshimura et al.

[11] 4,202,799
[45] May 13, 1980

[54] ORGANIC-HEAT-SENSITIVE SEMICONDUCTIVE COMPOUNDS

[75] Inventors: Susumu Yoshimura; Mutsuaki Murakami; Midori Shinoda, all of Kawasaki, Japan

[73] Assignee: Matsushita Electric Industrial Co., Ltd., Kadoma, Japan

[21] Appl. No.: 915,259

[22] Filed: Jun. 13, 1978

[30] Foreign Application Priority Data
Jun. 17, 1977 [JP] Japan .................................. 52-72419

[51] Int. Cl.$^2$ ............................................ H01C 31/00
[52] U.S. Cl. ................................. 252/500; 338/22 SD
[58] Field of Search ................. 252/500; 546/275, 330

[56] References Cited
U.S. PATENT DOCUMENTS
3,334,109  8/1967  Harris .............................. 252/500 X Primary Examiner—E. Suzanne Parr
Attorney, Agent, or Firm—Lowe, King, Price & Becker

[57] ABSTRACT

Organic heat-sensitive semiconductive compounds composed of (N-n-propylpyridinium) (7,7,8,8-tetracyanoquinodimethane)$_2$ and (N-n-propylthiazolium) (7,7,8,8-tetracyanoquinodimethane)$_2$ or (N-n-butylthiazolium) (7,7,8,8-tetracyanoquinodimethane)$_2$. The compound using the propylthiazolium component exhibits phase transition phenomena in a wide range of temperatures lower than that of the basic component of (N-n-propylpyridinium) (TCNQ)$_2$. While, the compound using the butylthiazolium component shows inherent temperature hystereses different from that of the basic component.

5 Claims, 15 Drawing Figures

ORGANIC-HEAT-SENSITIVE SEMICONDUCTIVE COMPOUNDS

This invention relates to organic semiconductive materials showing reversible phase transition phenomena and more particularly, to heat-sensitive ion radical or charge transfer complex materials of the type which contains 7,7,8,8-tetracyanoquinodimethane(hereinlater referred to simply as TCNQ) as electron acceptor. The present invention also relates to semiconductive compositions and heat sensitive elements using the heat sensitive materials of the type just mentioned.

As is well known in the art, many studies have been directed to the phase transition of organic semiconductive materials including TCNQ complex salts. Several compounds have been found to show reversible or irreversible phase transition phenomena. These phase transition phenomena are generally observed as anomalities in resistance-temperature characteristics at the phase transition temperatures. There have been heretofore proposed several heat-sensitive elements or temperature-detecting elements utilizing these anomalities of the organic semiconductive materials. Typical of the semiconductive materials showing such anomal resistance-temperature characteristics is triphenylmethylphosphonium(TCNQ)$_2$, which is discussed in detail by Kepler et al(J. Chem. Phys., Vol. 39, page 1311(1963)). Another example of such material is N-n-propylpyridinium(TCNQ)$_2$, which we proposed in our prior Japanese Laid-open specification No. 45685/1976. These TCNQ compounds have a rapidly varying resistance in a temperature range above a normal temperature. Tetrathiofulvalenium(TCNQ) is known to have a rapidly varying resistance at a much lower temperature, i.e. the phase transition occurs at $-215°$ C.

With a very few exceptions, the crystals of the TCNQ salts are characterized in that TCNQ molecules are stacked to form chains therebetween. The binding force between the TCNQ molecules in the vertical direction is very weak, so that the physical properties of the TCNQ crystals is considered to be those of one-dimensional crystals. Such one-dimensional crystals are in most cases physically unstable and susceptible to changes in crystalline arrangement, depending on temperature or pressure, resulting frequently in a phase transition.

One of the reasons why the phase transition of the TCNQ salts or other organic semiconductive materials have attracted special attention from a solid-state-chemical or electronic aspect is due to a fact that such salts or materials are relatively easy in varying phase transition parameters. This is because it is much easier in the case of organic crystals to introduce impurities or compounds of a similar type into the crystals than in the case of inorganic crystals or compounds so as to cause the disorder in the crystals. By the introduction, the phase transition temperature can be arbitrarily varied to an extent. There are known several organic compounds of like compounds including compounds of(triphenylmethylphosphonium) (TCNQ)$_2$ and (triphenylmethylarsonium) (TCNQ)$_2$ and of (tetrathiafluvalene) (TCNQ) and (tetraselenafulvalene) (TCNQ). It has been found that, in these organic compounds, their phase transition temperature can be varied simply by varying the composition. However, the former compound is disadvantageous in that its rate of change in resistivity is small, while the latter compound is too low in phase transition temperature.

It is an object of the present invention to provide novel heat-sensitive organic semiconductive compounds which contain tetracyanoquinodimethane as electron acceptor.

It is another object of the present invention to provide novel heat-sensitive organic semiconductive compounds using (N-n-propylpyridinium) (TCNQ)$_2$ as a basic component.

It is a further object of the present invention to provide novel heat-sensitive organic semiconductive compounds which have phase transition temperatures shifted to lower level of temperature than that of (N-n-propylpyridinium) (TCNQ)$_2$ to an arbitrary extent depending on the composition of such compounds.

It is a still further object of the present invention to provide novel heat-sensitive organic semiconductive compounds which have a wider range of phase transition temperature than (N-n-propylpyridinium) (TCNQ)$_2$.

According to the present invention, there is provided an organic compound of an (N-n-propylpyridinium) (TCNQ)$_2$ complex salt and an (N-n-alkylthiazolium) (TCNQ)$_2$ complex wherein the alkyl moiety is propyl or butyl. By the reasons which will be described hereinafter, an organic compound of an (N-n-propylpyridinium) (TCNQ)$_2$ an (N-n-alkyl-thiazolium) (TCNQ)$_2$ expressed by the following formula (1) or (2) is preferred in the practice of the invention wherein x is in a range below 0.6, inclusive wherein y is in a range of from 0.2 to 0.8

The (N-n-propylpyridinium) (TCNQ)$_2$ complex salt is known to show anomalies in resistivity-temperature characteristics as will be described in detail hereinafter.

It has been found that when the (N-n-alkyl-thiazolium) (TCNQ)$_2$ complex salt is added to the (N-n-propylpyridinium) (TCNQ)$_2$ complex salt, the phase transition temperatures of the latter compound can be arbitrarily varied to a fair extent. When, for example, an (N-n-propylthiazolium) (TCNQ)$_2$ complex salt is added to the (N-n-propylpyridinium) (TCNQ)$_2$ complex salt to prepare an organic compound thereof, the phase transition temperatures of the latter compound at which the resistivity rapidly varies are shifted to a lower level of temperature in proportion to the amount of the former compound. This compound, using the (N-n-propylthiazolium) (TCNQ)$_2$, ensures a temperature detection in a wide range of temperatures of about 110° C. to 60° C. On the other hand, when an (N-n-butylthiazolium) (TCNQ)$_2$ complex salt is added to the (N-n-propylpyridinium) (TCNQ)$_2$ complex salt, the resulting compound is found to exhibit a much greater hysteresis of temperature in almost all proportions of the two components when undergoing the reversible phase transition phenomena.

These two kinds of the compounds are thus different in nature from each other but are both very useful when applied as heat-sensitive or timing elements.

The present invention will be described in detail with reference to the accompanying drawings, in which.

As described hereinbefore, the organic semiconductive compound or solid solution according to the invention is composed substantially of (N-n-propylpyridinium) (TCNQ)$_2$ and (N-n-propylthiazolium) (TCNQ)$_2$ or (N-n-butylthiazolium) (TCNQ)$_2$. These compounds are expressed by the following formulae, respectively.

(N-n-propylpyridinium) (TCNQ)$_2$ (N-n-propylthiazolium) (TCNQ)$_2$ (N-n-butylthiazolium) (TCNQ)$_2$ For the sake of brevity, the (N-n-propylpyridinium) (TCNQ)$_2$ will be hereinlater referred to as (NPPy) (TCNQ)$_2$, the (N-n-propylthiazolium) (TCNQ)$_2$ as (NPTh) (TCNQ)$_2$, and the (N-n-butylthiazolium) (TCNQ)$_2$ as (NBTh) (TCNQ)$_2$, respectively.

These starting TCNQ complex salts will be first described briefly. The TCNQ complex salts are all prepared in a similar manner by known techniques. In a broad aspect, it will suffice to mix TCNQ with an iodide of a corresponding organic cation, i.e., N-n-propylpyridinium, N-n-propylthiazolium or N-n-butylthiazolium iodide, in a solvent under mild refluxing conditions. The reaction solution is then allowed to stand overnight for crystallization at a suitable temperature of about 5° C. to 15° C. and the resulting crystals are separated and washed with the solvent and then with ethyl ether. Acetonitrile, acetone and methylene chloride are usable as solvent. The washed crystals are recrystallized in sufficiently purified solvent such as acetonitrile or acetone.

Figure 1:
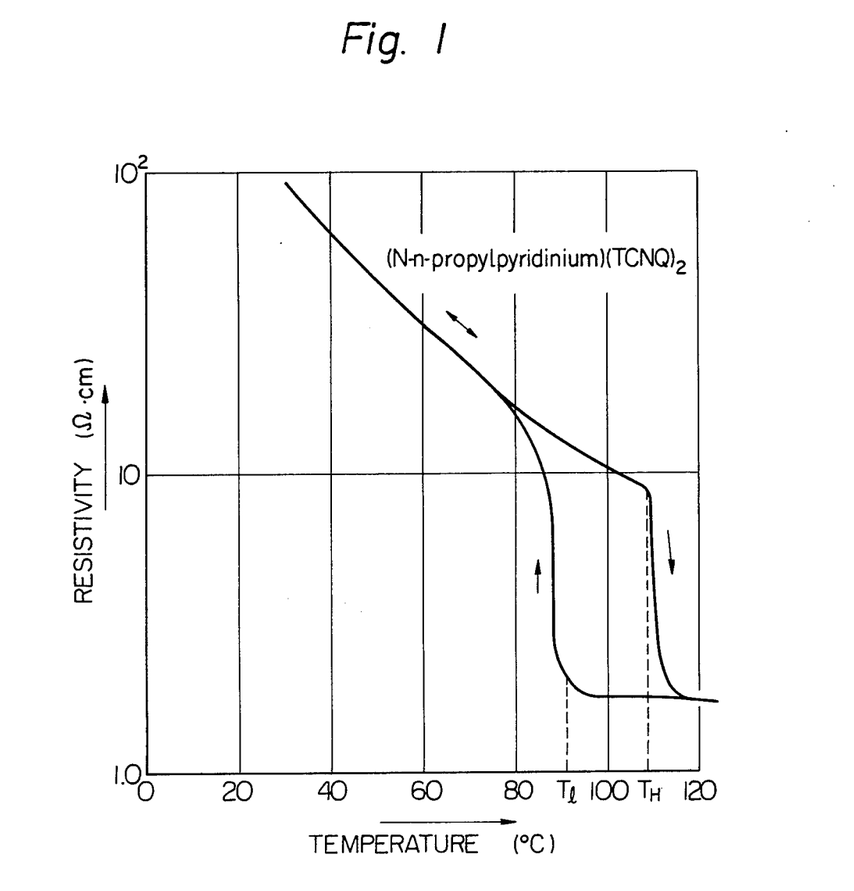
FIG. 1 is a graphical representation of specific resistance of (N-n-propylpyridinium) (TCNQ)$_2$ in relation to temperature.

As described hereinbefore, the (NPPy) (TCNQ)$_2$ which is a basic component for preparing the organic compound of the present invention is known to show anomalies in resistivity-temperature characteristics, or reversible phase transition phenomena. With reference to FIG. 1, there are shown typical resistivity-temperature characteristics of a press molding of (NPPy) (TCNQ)$_2$ powder, which are obtained by a four-probe method using silver paste. When the (NPPy) (TCNQ)$_2$ complex is heated gradually from a normal temperature, its resistivity is abruptly reduced down to about 1/10 at about 108° C., returning to the original level when cooled to about 90° C. or lower. That is, this phenomenon involves a temperature hystreresis. The resistivity-temperature characteristic cycle in the direction of arrows always takes place whenever the heating and cooling are repeated. Similarly, the arrows in other figures indicate the cycle of resistivity variation which occurs when a sample is heated and then cooled. When the phase transition temperature of the complex under temperature-increasing conditions is taken as $T_H$ and the phase transition temperature under temperature-decreasing conditions taken as $T_l$, as shown in FIG. 1, $T_H = 108°$ C. and $T_l = 90°$ C. The hysteresis temperature is defined as $\Delta T = T_H - T_l$, which is thus 18° C. in this case.

Figure 2:
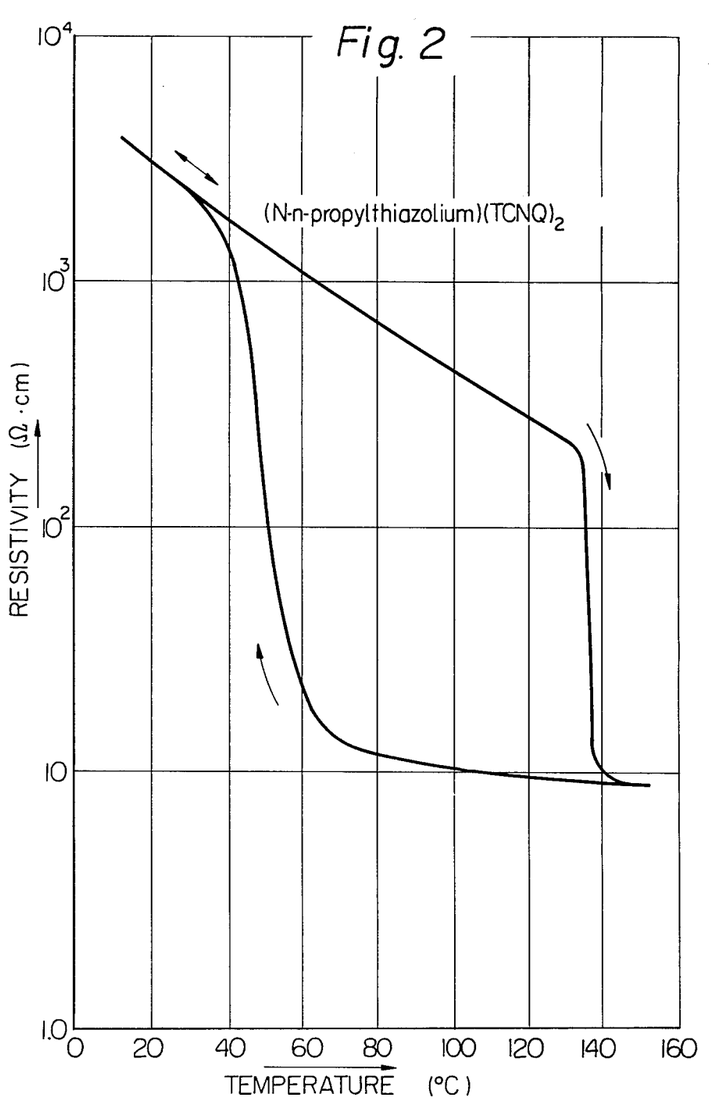
FIG. 2 is a graphical representation of specific resistance of (N-n-propylthiazolium) (TCNQ)$_2$ in relation to temperature.

The (NPTh) (TCNQ)$_2$ complex salt which is one component to be combined with the (NPPy) (TCNQ)$_2$ complex salt has resistivity-temperature characteristics as shown in FIG. 2. From the figure, it will be seen that the hysteresis temperature is very great. This complex salt has phase transition temperatures, $T_H$ of 128° C. and $T_l = 63°$ C. and a hysteresis temperature, $\Delta T$ of 65° C.

Figure 3:
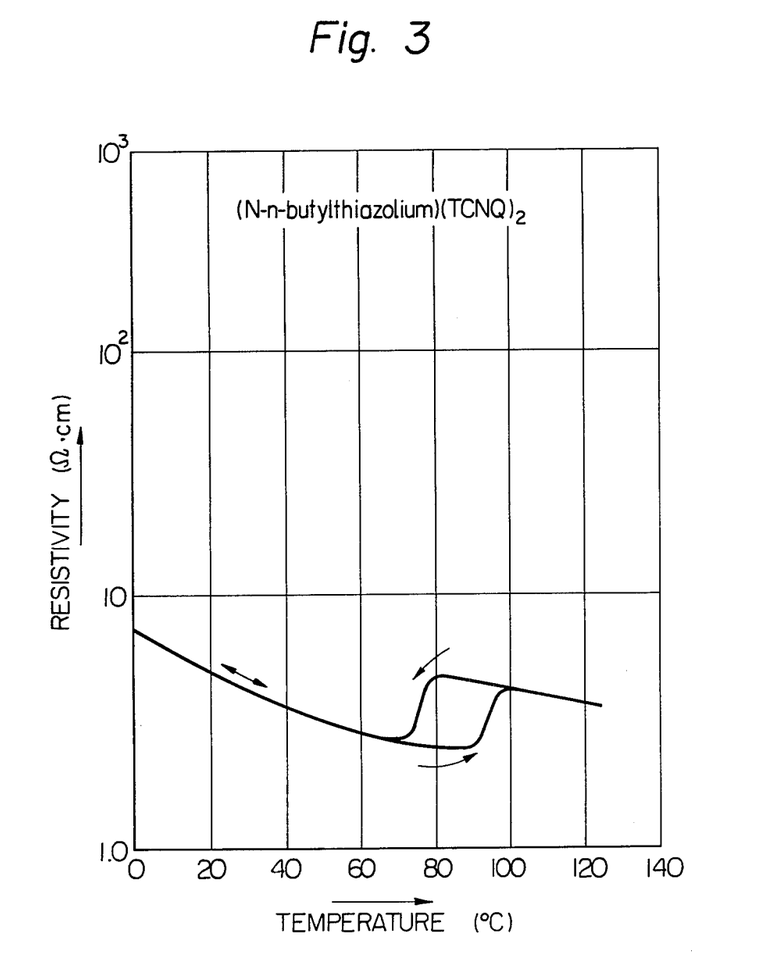
FIG. 3 is a graphical representation similar to FIG. 2 but for (N-n-butylthiazolium) (TCNQ)$_2$.

The (NBTh) (TCNQ)$_2$ complex salt which is another component to be added to the (NPPy) (TCNQ)$_2$ complex salt for preparing another type of organic compound of the invention also exhibits phase transition phenomena and is characterized in that its resistivity increases with an increase of temperature. That is, this complex salt has a so-called PTC(Positive Temperature Coefficient) characteristics. These characteristics are shown in FIG. 3. The phase transition temperatures expressed in terms of $T_H$ and $t_l$ are 100° C. and 90° C., respectively.

The organic compound of the (NPPy) (TCNQ)$_2$ complex salt and the (N-alkylthiazolium) (TCNQ)$_2$ complex salt according to the invention will be described. These compounds contain two cation components and one anion component and may thus be called ternary compounds. The ternary compounds are different from each other in resistivity-temperature characteristics. By addition of the (NPTh) (TCNQ)$_2$ complex salt to the (NPPy) (TCNQ)$_2$ complex salt, the rapidly varying resistivities are shifted to a lower level of temperature than that of the (NPPy) (TCNQ)$_2$ complex salt. The shifting level depends on the amount of the (NPTh) (TCNQ)$_2$ complex salt. The compound of the (NPPy) (TCNQ)$_2$ and (NPTh) (TCNQ)$_2$ complex salts ensures a temperature detection in a wide range of 110° C. to 60° C. or lower and has thus a wide variety of applications. On the other hand, the compound of the (NPPy) (TCNQ)$_2$ and (NBTh) (TCNQ)$_2$ complex salts has much greater hysteresis temperatures, which vary depending on the amount of the (NBTh) (TCNQ)$_2$ complex salt.

The synthetic methods and resistivity-temperature characteristics of those compounds according to the present invention are given in more detail below Compound of (NPPy) (TCNQ)$_2$ and (NPTh) (TCNQ)$_2$ or (NPPy)$_{1-x}$(NPTh)$_x$(TCNQ)$_2$ (1) Synthesis The synthesis of the compound is feasible by several methods including a co-reprecipitation, a recrystallization and a powdering and heating technique. These methods are described in order.

(a) Co-reprecipitation (NPPy) (TCNQ)$_2$ and (NPTh) (TCNQ)$_2$ which have been prepared by a known method as described hereinbefore are weighed in a desired mixing ratio, and dissolved in acetonitrile at about 80° C. Preferably, the complex salts are dissolved in concentrations as high as possible and, most preferably, a saturated solution is prepared. The solution is then dropped into water maintained at 0°–5° C. in an amount at least ten times as great as that of the solution. The water used should be as pure as possible and be violently agitated. After completion of the dropping, the resulting precipitate is separated by a suitable means such as a glass filter, repeatedly washed with pure water and dried. In the method, other solvents for dissolving the complex salt may be used, apart from acetonitrile, including dimethylformamide, acetone, methyl alcohol and the like. Instead of water, ethyl ether and hexane may be likewise used.

(b) Recrystallization

The (NPPy) (TCNQ)$_2$ and (NPTh) (TCNQ)$_2$ complex salts which have been prepared by a known method are dissolved in acetonitrile in a desired mixing ratio and recrystallized by a known technique. Acetone, ethylene chloride and methyl alcohol may be used as the solvent for the recrystallization.

(c) Powdering and Heating Method

The (NPPy) (TCNQ)$_2$ and (NPTh) (TCNQ)$_2$ complex salts weighed in a desired mixing ratio are powdered in a suitable means such as a mortar and then heated at 140° C. for at least 30 minutes.

In the synthetic methods (a) and (b), it is necessary to heat the resulting product at a temperature above 130° C. for a time above 30 minutes, whereupon it is converted into a compound having inherent reversible resistivity-temperature characteristics.

When the products composed of the (NPPy) (TCNQ)$_2$ and (NPTh) (TCNQ)$_2$ complex salts and obtained by the above three methods are each subjected to an elementary analysis, it has been found that the products contain the (NPTh) (TCNQ)$_2$ complex salt approximately in such a ratio as initially weighed when calculated on the basis of the sulfur component contained in the complex salt. Further, the X-ray diffraction analysis has revealed that the products obtained by any of the above methods do not yield such a simple pattern as that obtained by superposing the patterns of the (NPPy) (TCNQ)$_2$ and (NPTh) (TCNQ)$_2$ complex salts but show a pattern completely different from those of the complex salts. Thus, the products are believed to be compounds, not mere mixtures of the two complex salts.

(2) Resistivity-temperature Characteristics

The compound is powdered and press molded at a normal temperature to give a rod having a diameter of 3 mm and a length of about 10 mm. The rod is provided with four probes by use of a gold wire and its resistivity is measured by passing an electric current of 100–10 μA between the two terminals at the outside and measuring a voltage variation between the two terminals at the inside in relation to temperature.

Figure 4:
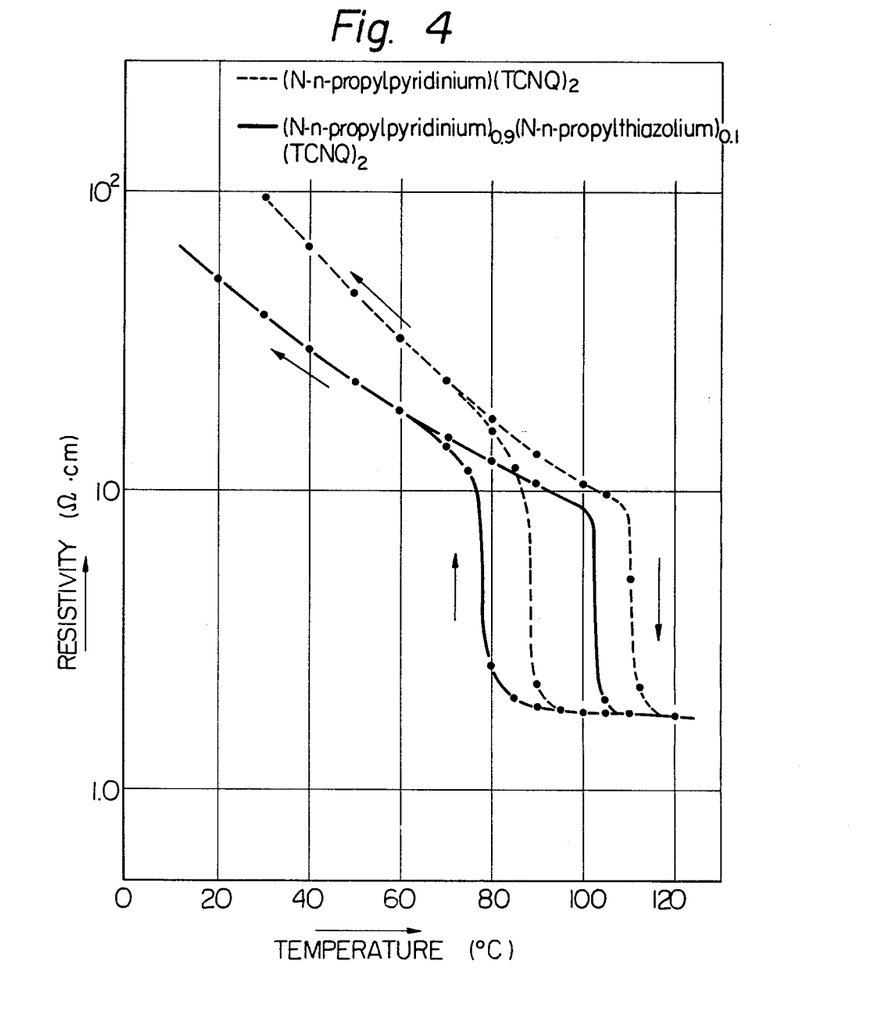
FIG. 4 is a graphical representation of specific resistance of (N-n-propylpyridinium)$_{0.9}$(N-n-propylthiazolium)$_{0.1}$(TCNQ)$_2$ according to the invention in relation to temperature.

FIG. 4 shows the resistivity-temperature characteristic curves in which the curve indicated by dotted line is for $(NPPy)(TCNQ)_2$ and that indicated by solid line is for $(NPPy)_{0.9}(NPTh)_{0.1}(TCNQ)_2$. As will be seen from the figure, with the $(NPPy)(TCNQ)_2$ complex salt, the resistivity abruptly varies at or in the vicinity of 108° C. and 90° C. When the $(NPPy)(TCNQ)_2$ complex salt is added with 10 mole % of $(NPTh)(TCNQ)_2$, its temperatures at which the resistivity abruptly varies are shifted to 101° C. and 80° C. under temperature-increasing and temperature-decreasing conditions, respectively. The degree of the shifting is approximately directly proportional to the quantity of the added $(NPTh)(TCNQ)_2$.

Figure 5:
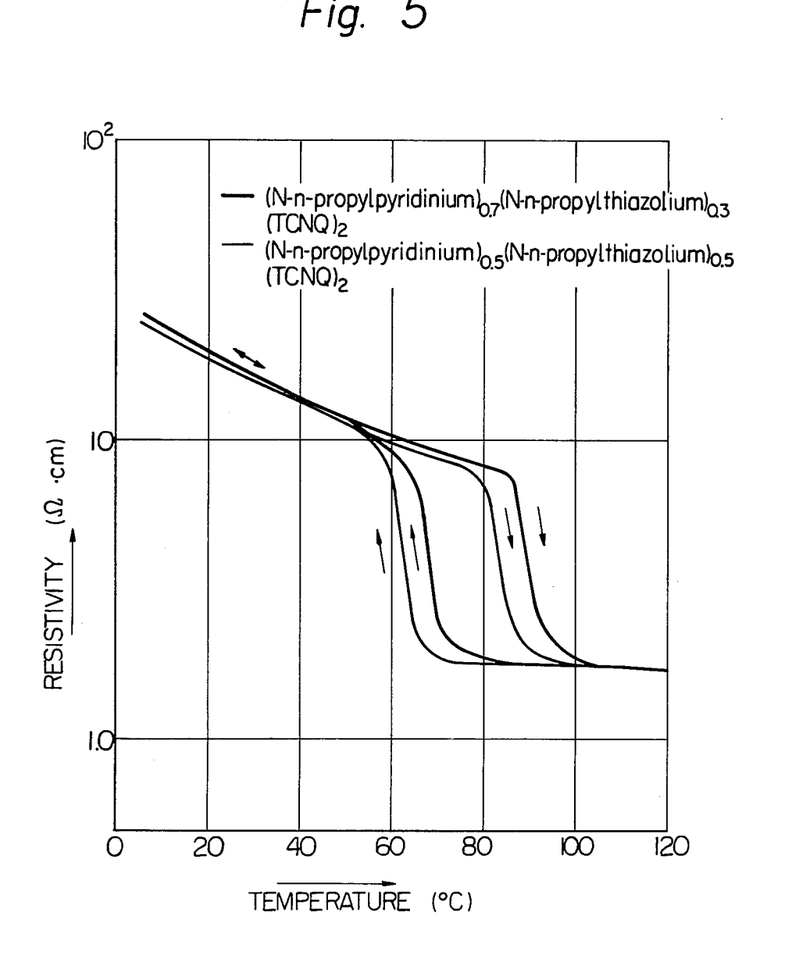
FIGS. 5 and 6 are graphical representations similar to FIG. 4.

FIG. 5 also shows resistivity-temperature characteristic curves in which the curve indicated by thick line is for $(NPPy)_{0.7}(NPTh)_{0.3}(TCNQ)_2$ and that indicated by thin line is for $(NPPy)_{0.5}(NPTh)_{0.5}(TCNQ)_2$. The results of the figure show that when the $(NPTh)(TCNQ)_2$ complex salt is added in amounts above 30 mole %, the degree and sharpness of resistivity change become slightly poorer. With $x=0.3$, the $T_H$ and $T_I$ of the compound are found to be 87° C. and 72° C., respectively. With $x=0.5$, the $T_H$ and $T_I$ are, respectively, 77° C. and 67° C. Upon comparing with the $(NPPy)(TCNQ)_2$, the phase transition temperatures are shifted to lower level of temperature by 20° C. or more.

Figure 6:
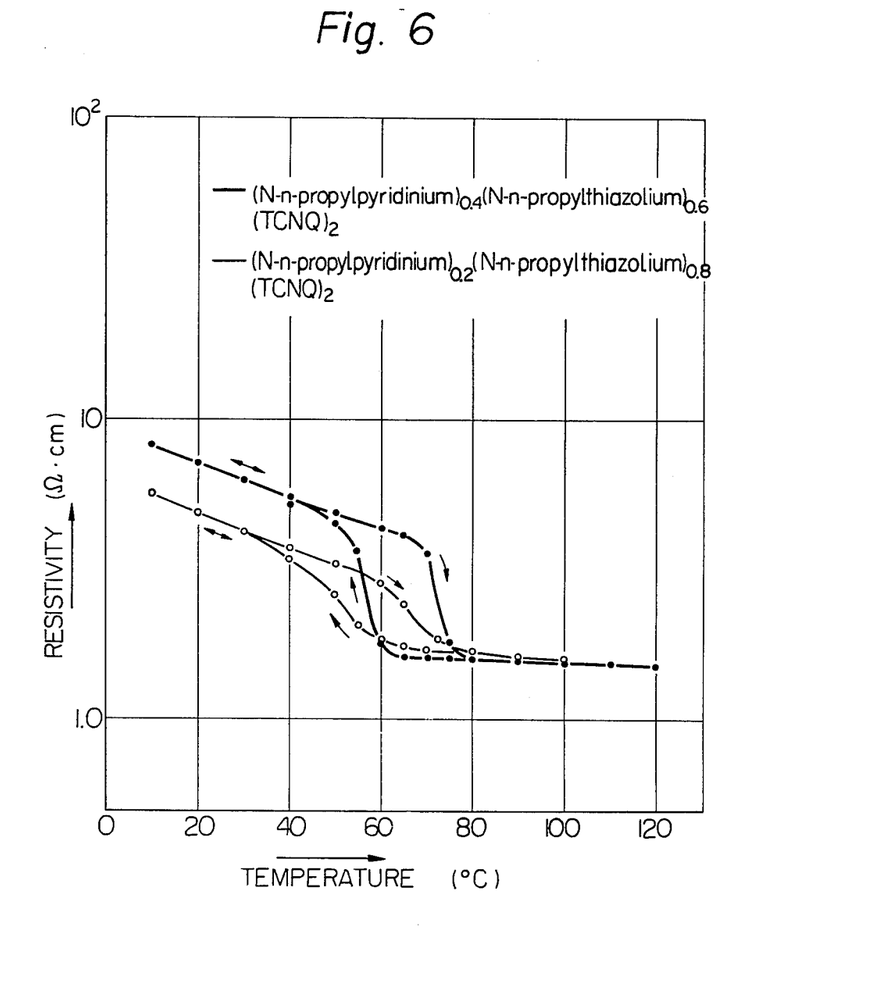

FIG. 6 shows further resistivity-temperature characteristic curves in which the curve indicated by thick line is for $x=0.6((NPPy)_{0.4}(NPTh)_{0.6}(TCNQ)_2)$ and that indicated by thin line is for $x=0.8((NPPy)_{0.2}(NPTh)_{0.8}(TCNQ)_2)$. The phase transition temperatures $T_H$ and $T_I$ with $x=0.6$ are found to be 70° C. and 60° C., respectively, and, with $x=0.8$, are found to be 60° C. and 55° C., respectively. Though the phase transition temperatures are shifted to a much lower level, the degree and sharpness of the resistivity change are found to be fairly poor. The compound of $x=8$ or greater is considered unsatisfactory in a practical sense.

Figure 7:
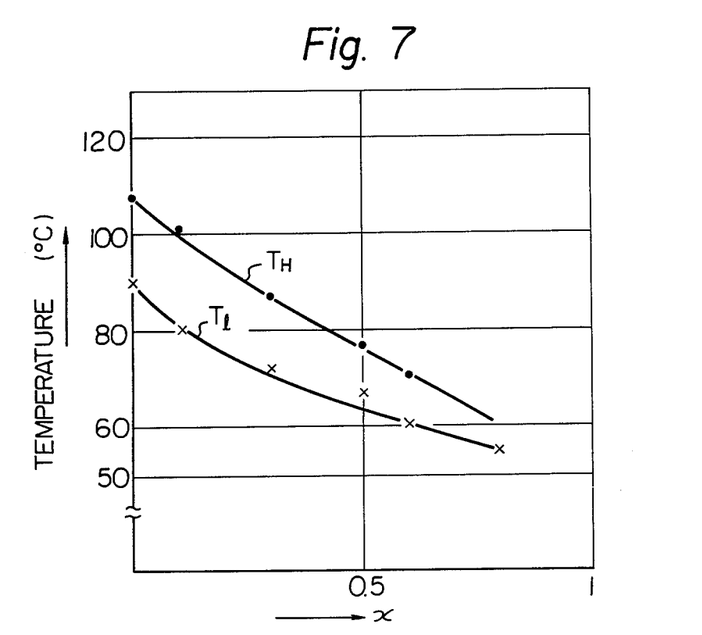
FIG. 7 is a graphical representation of variations in phase transition temperature in relation to variation in x of (N-n-propylpyridinium)$_{1-x}$(N-n-propylthiazolium)$_x$(TCNQ)$_2$.

In FIG. 7, there are shown the curves of the variations of $T_H=T_I$ in relation to x of the compound, from which it will be understood that an increase of x results in decreases of $T_H$ and $T_I$.

Figure 8:
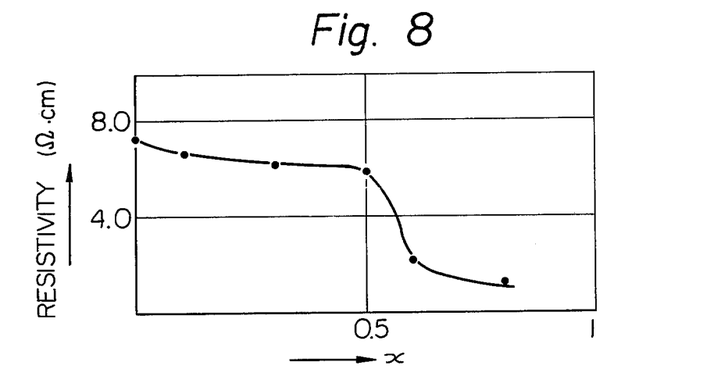
FIG. 8 is a graphical representation of a variation in specific resistance in relation to variation in x of (N-n-propylpyridinium)$_{1-x}$(N-n-propylthiazolium)$_x$(TCNQ)$_2$.

The resistivity change at the phase transition temperature $T_H$ in relation to variation in x is clearly shown in FIG. 8, from which it will be seen that the resistivity change becomes very small when x is greater than 0.6. Thus, the $(NPPy)_{1-x}(NPTh)_x(TCNQ)_2$ compound is preferred, as heat-sensitive material, to have a value of x in the range below 0.6, inclusive, and most preferably in the range of from 0.05 to 0.6 since the effect of addition of the $(NPTh)(TCNQ)_2$ complex salt clearly appears at a value of x of 0.05.

Compound of $(NPPy)(TCNQ)_2$ and $(NBTh)(TCNQ)_2$ or $(NPPy)_{1-y}(NBTh)_y(TCNQ)_2$

(1) Synthesis

The preparation of this compound is also feasible by any of the methods described with regard to the $(NPPy)_{1-x}(NPTh)_x(TCNQ)_2$ compound. The preparation by coreprecipitation will be particularly described. 37 g of $(NPPy)(TCNQ)_2$ and 11.5 g of $(NBTh)(TCNQ)_2$ are dissolved in 125 ml of dimethylformamide and maintained at 80° C. Then, 10 l of water maintained at 0°–5° C. is well stirred by means of a stirrer, into which the dimethylformamide solution is dropped from a dropping funnel. The resulting fine crystals dispersed in the water are collected by use of a glass funnel, washed sufficiently with water and ether, and vacuum dried at a temperature of 65° C. for about 8 hours. The thus obtained crystals contain lumps of crystals as secondary particles, so that they are reduced to powder in a mortar and shaped into pellets. The pellet product has been found to be an compound expressed by $(NPPy)_{0.77}(NPTh)_{0.23}(TCNQ)_2$ and has a specific resistance of $2.0\Omega.m$ at a normal temperature. When thermally treated at temperatures above 130° C. for a time above 30 minutes, the compound is converted to have a specific resistance of $220\Omega.cm$ and exhibits inherent reversible phase transition phenomena.

(2) Resistivity-temperature Characteristics

Figure 9:
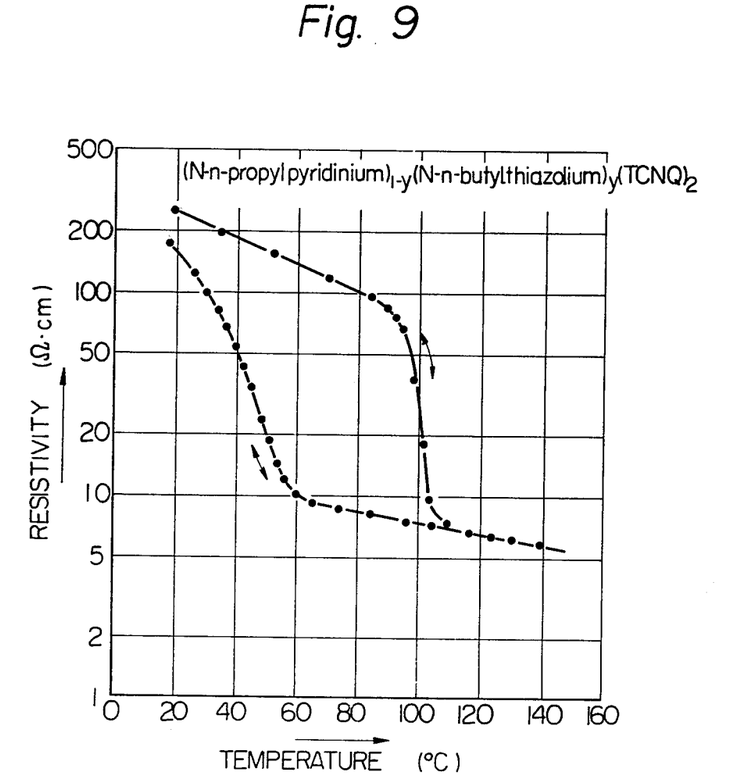
FIG. 9 is a graphical representation for (N-n-propylpyridinium)$_{0.7}$(N-n-butylthiazolium)$_{0.23}$(TCNQ)$_2$.

In FIG. 9, there are shown resistivity-temperature characteristic curves of the compound obtained in the synthesis. Similarly to the case of the $(NPPy)_{1-x}(NPTh)_x(TCNQ)_2$, the resistivity-temperature characteristics are measured by a four-probe method using gold wires and a rod-like molding of 3 mm in diameter and 10 mm in length. As a result, it has been found that the phase transition parameters obtained are as follows: $T_H=95°$ C., $T_I=56°$ C.; and $T=39°$ C. Further, the specific resistance at 145° C. is found to be $6.2\Omega.cm$. The resistivity at the phase transition temperature $T_H$ is reduced down to just 1/10.

Figure 10:
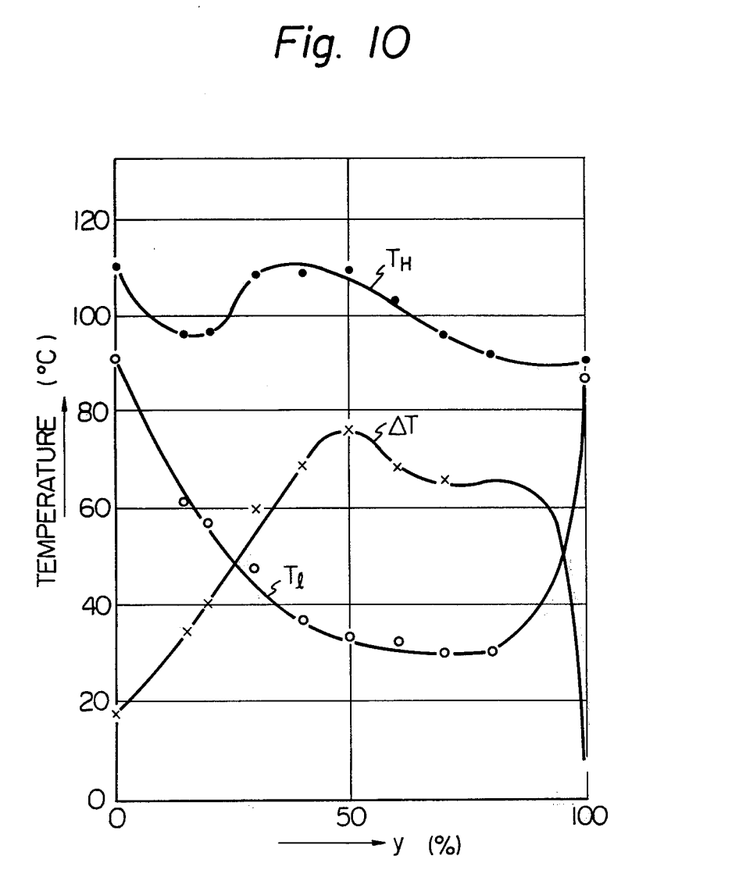
FIG. 10 is a graphical representation of variations in phase transition temperatures in relation to variation in y of (N-n-propylpyridinium)$_{1-y}$(N-n-butylthiazolium)$_y$(TCNQ)$_2$.

Then, the hysteresis temperature is measured in relation to variation in y of the $(NPPy)_{1-y}(NBTh)_y(TCNQ)_2$, which has been prepared by the coreprecipitation method. The results are shown in FIG. 10, from which it will be clear that the hysteresis temperature $\Delta T$ is greater than that of the basic $(NPPy)(TCNQ)_2$ complex salts except the case where the $(NBTh)(TCNQ)_2$ content approaches 100 mole %. The hysteresis temperature as great as 40° C. or greater appears when the content of the $(NBTh)(TCNQ)_2$ by mole % is between 20 and 80. With the content of $(NBTh)(TCNQ)_2$ below 10 mole %, the compound has a tendency similar to $(NPPy)(TCNQ)_2$ with regard to the resistivity-temperature characteristics. Especially when the content of $(NBTh)(TCNQ)_2$ is in the range of from 20 to 80 mole %, the phase transition temperatures $T_H$ and $T_I$ at which the resistivity abruptly decreases and increases, respectively, are completely different from those of $(NPPy)(TCNQ)_2$ and $(NBTh)(TCNQ)_2$, respectively, with the hysteresis temperature being much higher. Thus, the $(NPPy)_{1-y}(NBTh)_y(TCNQ)_2$ compound is preferred to have y in the range of from 0.2 to 0.8 though the alloy having a value of y outside the above range is also usable. As will be understood from the characteristic behavior of the compound, the compound is believed to be different from a mere mixture of (NPPY)(TCNQ)$_2$ and (NBTh)(TCNQ)$_2$ or from the individual complex salts. This is mainly due to the difference in crystalline structure. The reason why such great hystereses are induced is not known theoretically. Though not known theoretically, the (NPPy)$_{1-y}$(NBTh)$_y$(TCNQ)$_2$ compound exhibits an abnormally great hysteresis temperature, the phase transition temperature $T_H$ varying from 90° C. to 110° C. with a variation of y and the phase transition temperature $T_l$ varying from 60° C. to 30° C. when $0.2 \leq y \leq 0.8$. The hysteresis temperature $\Delta T$ is 40° C. at a minimum and 75° C. at a maximum within the above range of y.

Two kinds of the organic semiconductive compounds which have been described hereinbefore may be added with conventionally employed additives to produce resistors having a desired level of resistivity. For example, graphite or metal powder is used to lower the resistivity of the compound according to the invention. The addition of the above-mentioned additives makes it possible to cause the temperature coefficient of resistance value close to zero. In order to increase resistivity of the compound, inorganic materials such as cement or a variety of polymers are useful.

Further, the organic compound of the invention may be improved in physical properties by adding thereto a binder resin which is unreactive with the compound. The binder resin is generally used in an amount of 5 to 50% by weight of a final composition. Larger amount will impair the heat-sensitive property of the compound while smaller amount will not assist in improving the physical properties. Examples of usable binder resins include ethylene-vinyl acetate copolymer, polyvinylbutyral, polyvinylpyrrolidone, polyurethane, polycarbonate, ethyl cellulose, chlorinated rubber, vinyl chloride-vinyl acetate copolymer, polyvinylidene chloride, polyvinyl chloride, polyvinyl formal, polymethyl methacrylate, chlorinated polypropylene, nitrocellulose resin, cyclized rubber and the like.

According to a specific feature of the invention, the organic compound of the invention are readily shaped into desired forms, i.e. into discs by press molding, into thick films by screen printing, into thin films by vacuum evaporation, etc., whichever is suitable as heat-sensitive or timing element.

The following discussion deals with applications, as heat-sensitive or timing element, of the organic compound of the invention.

Although the reason why the phase transition takes place is not known at the present stage of our investigation, the sluggish transient phenomenon may be utilized to make electronic timing or heat-sensitive element. The timing or heat-sensitive element using the compound of the invention may be provided in the form of a small press molding, or a film strip formed on a substrate, with a pair of electrodes attached to the molding or film at a distance from each other, and a resin covering enclosing the press molding or film and the pair of electrodes. This element may be incorporated in an indirectly heating unit provided with one or more heaters.

Figure 11:
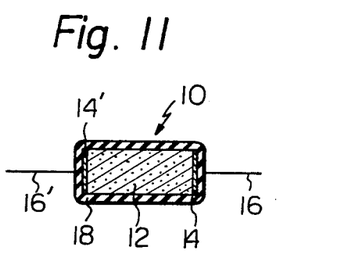
FIG. 11 is a schematical sectional view of a heat-sensitive element of a disc type using heat-sensitive semiconductive materials of the invention.

FIG. 11 shows generally at 10 a timing element using a press molding of the organic compound of the invention. The element 10 includes a press-molded compound 12, a pair of electrodes 14 and 14' provided at opposite sides of the press molding 12 in contact therewith, lead wires 16 and 16' connected with the pair of electrodes 14 and 14', respectively, and a resin covering 18 enclosing the entire assembly of the press molding 12 and the pair of electrodes 14 and 14'. In this instance, the compound is powdered by co-reprecipitation or grinding. Then, the powder is pressed under a pressure of about 5 tons/cm$^2$ at a temperature of 150° C. into a desired form such as cylinder, angled pillar or the like. Upon shaping, the compound may be mixed with any additives. For examples, small amounts of polymers may be added to improve the molding in physical strengths. The electrode is usually made of carbon powder added with polymer and is attached to the molding simultaneously with the shaping. From the electrode extends a lead wire by use of silver paste.

Figure 12:
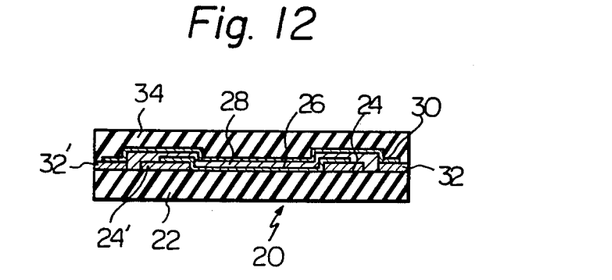
FIG. 12 is a schematical sectional view of another heat-sensitive element of the invention.

FIG. 12 shows an indirectly heated heat-sensitive timing element 20. The element 20 includes an insulating heat-resistant substrate 22, a pair of electrodes 24 and 24', and a resistor or carbon film 26 formed on the substrate 22 in contact with the pair of electrodes 24 and 24' at the opposite ends thereof. The pair of electrodes 24 and 24' and the resistor film 26 are covered with an insulating layer 28 to electrically insulate an organic heat-sensitive compound layer 30 from the resistor 26. The compound layer 30 is a thick film obtained by screen printing. Designated at 32 and 32' are a pair of electrodes for the compound layer 30. The upper surface of the substrate is entirely covered with a resin covering 34 for complete insulation.

The present invention will be particularly illustrated by way of the following examples.

EXAMPLE 1

This Example illustrates film formation of the (NPPy)$_{1-y}$(NPTh)$_x$(TCNQ)$_2$ by vacuum evaporation.

An evaporation source (such as a tungusten bucket or a molybdenum boat) was maintained at a temperature of 220° C.±2° C., to which was charged powder of the organic compound. The powder used was obtained by, for example, a co-reprecipitation method, to have an average size of 0.5–1μ. A substrate for evaporation was placed at a distance of about 10 cm from the source and was maintained at a temperature above 80° C. so as to avoid the separation of once deposited substance. By the vacuum evaporation for 10 to 20 seconds, dark brown or black uniform film exhibiting an interference fringe was obtained. The film thickness was controlled by way of the evaporation time or the distance between the evaporation source and the substrate. When the compound was vacuum evaporated to a thickness of 1μ or greater, the film surface became rough and gave rather poor electrical characteristic.

The phase transition temperatures of the evaporated film were shifted to lower level than those of (NPPy)(TCNQ)$_2$ as shown in FIG. 4.

The heat-sensitive compound vacuum evaporated on a substrate with small heat capacity was capable of heat detection with high sensitivity.

EXAMPLE 2

This Example illustrates fabrication of thick film element using (NPPy)$_{0.9}$(NPTh)$_{0.1}$(TCNQ)$_2$ by a printing method.

The compound was prepared by a co-reprecipitation method as described in Synthesis of (NPPy)$_{1-x}$(NPTh)$_x$(TCNQ)$_2$ to have an average particle size of 0.5–1μ. The powder and an ethylene-vinyl acetate copolymer (having a vinyl acetate content of 30%) were dispersed in a solvent such as dichlorobenzene. The dispersion was printed on a ceramic substrate in a desired pattern by a screen printing. The substrate had been previously provided with a pair of electrodes at opposite ends of the substrate. The printed substrate was then treated at a temperature below 160° C. for several hours. Lead wires were connected to the electrodes on the film. Finally, the substrate was covered with a resin covering for insulation.

Figure 13:
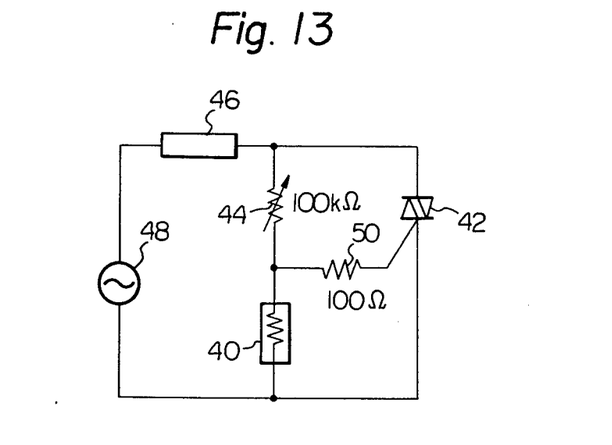
FIG. 13 is a circuit diagram using a semiconductive material of the invention applied as a temperature switch.

This thick film element was applied as a temperature switch. For the above purpose, a circuit of FIG. 13 was used in which designated at 40 is the heat-sensitive element of the invention which serves to control a gate current of a thyrister 42. A variable resistance 44 was pre-set at a predetermined value so that the thyrister 42 became opened at a temperature below $T_H$ or 101° C. and short-circuited at a temperature above $T_H$. When the thyrister 42 was rendered conductive, electric current was fed to a load 46 to actuate a suitable means such as a lump or buzzar. Indicated at 48 and 50 are a power supply and a resistance, respectively.

The feature of this circuit is that the circuit is closed when the heat-sensitive element is heated to above the temperature $T_H$ or 101° C., and opened at temperatures below $T_I$ or 80° C., not below $T_H$. That is, the temperature hysteresis of the alloy as shown in FIG. 4 is effectively utilized to make a switch of a safety type.

EXAMPLE 3

This Example illustrates fabrication of a thick film resistor element using $(NPPy)_{1-y}(NBTh)_y(TCNQ)_2$ by a printing technique such as screen printing or gravure printing, and also of a disc type element.

The powder of the compound was prepared by a co-reprecipitation method and passed through a sieve having openings of 44μ, thereby obtaining powder of a uniform size. Then, 50 g of the powder, 7.5 g of polyvinylbutyral and 400 ml of a mixture of butanol and butylcarbinol acetate in a mixing ratio of 1:1 were kneaded to make a paste. In this instance, the amount of the polymer could be varied in the range of from 5 to 50 g depending on the resistance value required. The paste was printed on a ceramic substrate by use of a 300 mesh stainless screen.

For making a disc type element as shown in FIG. 11, the same powder as used above was mixed with 5–10% by weight of a polymer as indicated hereinbefore. The mixture was shaped under a pressure of 5 tons/cm² at a temperature of 150° C. The electrodes were made of carbon powder admixed with a polymer. The disc type element had a diameter of 3 mm and a space between the electrodes of 1 mm. The resistance of the disc type element could be varied from 5 to 700Ω at a normal temperature While, the former thick film element (having a width of the compound layer of 2 mm and a space between electrodes of 2 mm) could be varied in the range of from 10 kΩ to 700 MΩ.

The both elements exhibited the type of resisitivity-temperature characteristics as shown in FIG. 9.

When a polymer of a specific type which is reactive with the compound was used or when materials for the covering or electrode are not suitable, the degree and sharpness of phase transition phenomenon were found to become poorer.

These elements are applicable as a temperature sensing device or an alarm device. For example, the $(NPPy)_{0.5}(NBTh)_{0.5}(TCNQ)_2$ compound was used to make the element. When the element was applied in an alarm circuit (not shown) and the alarming temperature is pre-set at 110° C., an alarming or safety device operates through a relay or a thyristor at temperatures over 110° C. The alarming is not cleared immediately after the temperature is lowered to 110° C. but is cleared only when the temperature reaches below 32° C.

EXAMPLE 4

The $(NPPy)_{1-y}(NBTh)_y(TCNQ)_2$ compound was used to make an indirectly heated thick film element of FIG. 12.

When a voltage of 100V was applied to the heater or resistor film 26, the resistance of the compound layer 30 was lowered from 500 KΩ to about 80 KΩ. Then, the heater was switched off. The resistance was not immediately returned to its original level. 3 hours after the switching-off, the resistance reached 480Ω. The time required for restoring its original level of 500 KΩ was about 10 hours. Needless to say, the returning time depends on the atmospheric temperature. When, for example, the heater temperature was held at 45° C., the time required for complete return was about 50 hours.

EXAMPLE 5

This Example illustrates timing characteristics of disc type elements of FIG. 11 using the $(NPPy)_{1-y}(NBTh)_y(TCNQ)_2$ complex salts.

Figure 14:
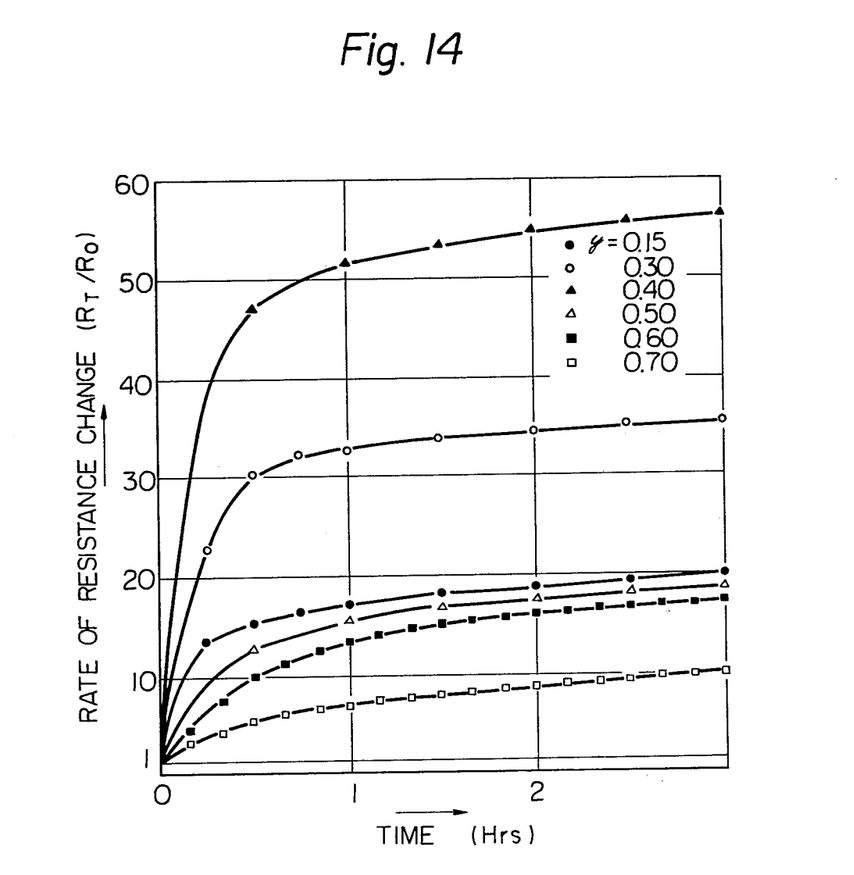
FIG. 14 is a graphical representation of variations in rate of resistance changes for different atmospheric temperatures in relation to time.

The elements using the compounds of different compositions ($0.15 \leq y \leq 0.7$) were made to measure at 17° C. the rate of resistance change in relation to time. The results are shown in FIG. 14, in which the abscissa indicates the time and the ordinate indicates the rate of resistance change, $R_T/R_O$ (where $R_T$ is a resistance at an ambient temperature (of 17° C.) and $R_O$ is a resistance at 140° C. As will be understood from the figure, the dependency of the rate of resistance change on the variation in y is considered to result from the combination of a phenomenon that the rate of resistance change decreases with an increase of y, and of an increase of a thermister constant in the vicinity of room temperature.

EXAMPLE 6

This Example illustrates timing characteristics of a disc type element of FIG. 11 using $(NPPy)_{0.4}(NBTh)_{0.6}(TCNQ)_2$.

Figure 15:
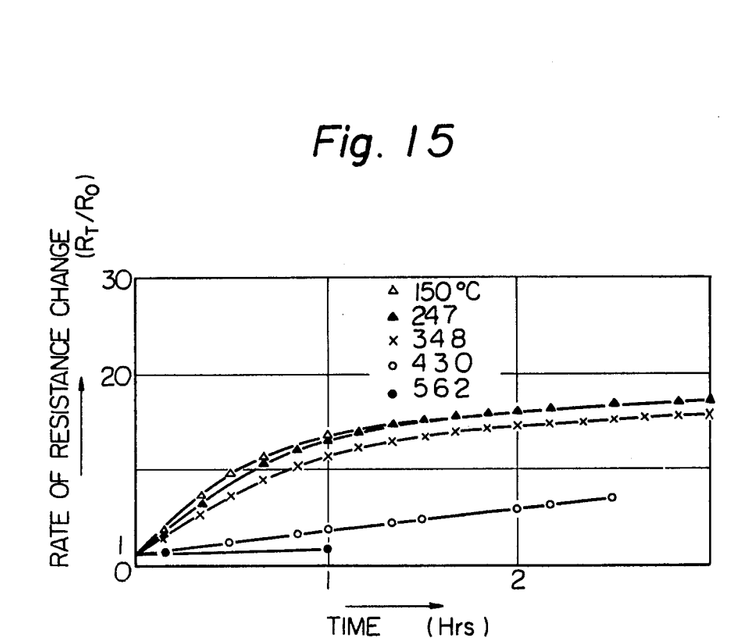
FIG. 15 is a graphical representation of variations in rate of resistance changes for different semiconductive compositions in relation to time.

The element was placed in atmospheres of different temperatures to determine the rate of resistance change for different temperatures in relation to time. The results are shown in FIG. 15, from which it will be clear that the rate of resistance change has little temperature dependency in the vicinity of 15°–35° C. The results of Examples 5 and 6 reveal that the $(NPPy)_{1-y}(NBTh)_y(TCNQ)_2$ compound exhibiting great temperature hysteresis characteristics functions as a delay switch when used to make an element including a control heater as shown in FIG. 12. The delay switch has wide utility in the field of timer for electric fan, delayed circuits for putting out lights, or intermittent switching for ventilation fan.

What is claimed is:

1. An organic heat-sensitive semiconductive compound of an (N-n-propylpyridinium)(TCNQ)$_2$ complex salt and an (N-n-alkylthiazolium)(TCNQ)$_2$ complex salt wherein the alkyl moiety is propyl or butyl.

2. An organic heat-sensitive semiconductive compound according to claim 1, wherein said alkyl moiety is propyl.

3. An organic heat-sensitive semiconductive compound according to claim 2, wherein said compound is

(N-n-propylpyridinium)$_{1-x}$(N-n-propylthiazolium)$_x$(7,7,8,8-tetracyanoquinodimethane)$_2$ expressed by the following formula wherein x is in a range below 0.6, inclusive.

4. An organic heat-sensitive semiconductive compound according to claim 1, wherein said alkyl moiety is butyl.

5. An organic heat-sensitive semiconductive compound according to claim 4, wherein said compound is (N-n-propylpyridinium)$_{1-y}$(N-n-butylthiazolium)$_y$(TCNQ)$_2$ expressed by the following formula wherein y is in a range of from 0.2 to 0.8.

* * * * *